United States Patent [19]

Briand

[11] Patent Number: 5,508,033
[45] Date of Patent: Apr. 16, 1996

[54] UTILIZATION OF ALGAE EXTRACT FOR THE PREPARATION OF PHARMACEUTICAL, COSMETIC, FOOD OR AGRICULTURAL COMPOSITIONS

[75] Inventor: Xavier Briand, Lezardieux, France

[73] Assignee: Societe d'Engrais Composes Mineraux et Amendments, Pontrieux, France

[21] Appl. No.: 388,639

[22] Filed: Feb. 14, 1995

Related U.S. Application Data

[63] Continuation of Ser. No. 231,956, Apr. 21, 1994, abandoned, which is a continuation of Ser. No. 859,703, Aug. 5, 1992, abandoned.

[30] Foreign Application Priority Data

Dec. 6, 1989 [FR] France ................... 89 16138

[51] Int. Cl.⁶ .............................. A61K 35/80; A61K 7/00
[52] U.S. Cl. ................. 424/195.1; 424/59; 424/701; 424/73; 424/74; 424/401; 426/590; 426/653; 514/846; 514/945
[58] Field of Search ........................ 424/401, 195.1, 424/70.1, 59, 73, 74; 514/846, 945; 426/590, 653

[56] References Cited

FOREIGN PATENT DOCUMENTS

| 0271133 | 6/1988 | European Pat. Off. |
| 2563414 | 4/1984 | France. |
| 2563414 | 10/1985 | France. |
| 2651617 | 5/1978 | Germany. |
| WO84/02652 | 7/1984 | WIPO. |

OTHER PUBLICATIONS

JPA 60–13709 (1985) Abstract.
Webster's New World Dictionary (1984) p. 506.
Manufacturing Chemist, vol. 57, No. 5, May, 1986, p. 30, London, GB; "Natural Products With Antibacterial Activity & Surface Active Properties On The Increase".

Patent Abstracts of Japan, vol. 9, No. 125 (C–283) [1848], 30 May 1985; and JP–A–60 13 609 (Nippon Carbide Kogyo K.K.) 24–01–1985 Resume.

Patent Abstracts of Japan, vol. 12, No. 433 (C–543) (3280), 15 Nov. 1988 and JP A, 63160567 (Shiraimatsu Shinyaku K.K.) 4 Jul. 1988 Resume.

W. Kern, et al. "Hagers Handbuch der Pharmazeutischen Praxis", 4 Ed., vol. IV Chemikalien und Drogen (Ci–G), 1973, Springer, (Berlin, DE), p. 1065, Paragraph Fucus vesiculosus.

S.T.N. Servers de bases de donnees, (Karlsruhe, DE), AN No. CA88(9):60081d, K. W. Glombitza, et al.: "Antibiotics From Algae. Part 21. Phlorotannin precursors in Dictyota Dichotoma".

S.T.N. Servers de bases de donnees, (Karlsruhe, DE), AN No. 90:265019, U. Woelwer–Rieck, et al.: "Alkaline Cleavage of Polymeric Phenols From Sargassum–Muticum and Pelvetia–Canaliculata".

Primary Examiner—Jyothsna Venkat
Attorney, Agent, or Firm—Stroock & Stroock & Lavan

[57] ABSTRACT

The present invention relates to the utilization of algae extracts obtained by extraction in liquid phase, or of at least one active substance isolated from such an extract or obtained by chemical synthesis, selected in particular among the fucols, polyfucols, diphloretols, polyphloretols, bifuhalols, polyfuhalols, phloretols, for the preparation of pharmaceutical, cosmetic, food or agricultural compositions with an anti-radical activity, particularly towards the superoxide radical. The algae used are brown, green or red macroscopic algae and in particular *Fucus vesiculosus*.

12 Claims, No Drawings

UTILIZATION OF ALGAE EXTRACT FOR THE PREPARATION OF PHARMACEUTICAL, COSMETIC, FOOD OR AGRICULTURAL COMPOSITIONS

This is a continuation of U.S. Ser. No. 08/231,956, filed Apr. 21, 1994, now abandoned, which is a continuation of U.S. Ser. No. 07/859,703, filed Aug. 5, 1992, now abandoned.

The present invention relates to a new utilization of algae extracts and finds a particular application in the preparation of pharmaceutical, cosmetic, food and agricultural compositions with anti-radical activity.

It is known that, because of their varied properties, algae extracts have been proposed in many pharmaceutical, cosmetic, food or agricultural applications.

The present invention is based on the unexpected discovery that the extracts of certain algae have an anti-radical activity towards the superoxide radical. It is known that the superoxide ions produced during oxidation reactions caused by molecular oxygen are very active and in particular attack proteins and nucleic acids.

Consequently, the invention proves to be particularly advantageous notably for protecting skin cells.

The invention finds another application in the preparation of food compositions, due to the protective power of the algae extracts towards polyunsaturated fatty acids.

The algae used according to the present invention are macroscopic green (Chlorophyceae), brown (Pheophyceae) and red (Rhodophyceae) algae.

Among the brown algae, the invention is particularly applicable to varieties of the Fucus, Pelvetia, Ascophyllum, Himanthalia, Laminaria, Sargassum species.

Among the red algae, the invention is particularly applicable to the varieties of the Chondrus, Mastocarpus or Girgatina, Palmaria, Porphyra, Ceramium and Gracilaria species.

Among the green algae, the invention is particularly applicable to the varieties of the Ulva, Enteromorpha and Codium species.

It has been found that all these algae have not the same degree of anti-radical activity.

Generally speaking, the brown algae have the highest anti-radical activity, and among them, it would seem that the Fucus, particularly *Fucus vesiculosus,* is currently the most advantageous.

Other varieties of algae suitable to be used according to the invention are *Ascophyllum nodosum, Pelvetia canaliculata,* Enteromorpha, *Palmaria palmata, Sargassum muticum, Ceramium rubrum, Gracilaria verrucosa, Ulva lactuca; Laminaria digitata;* Codium.

The algae extracts used according to the invention can be prepared by conventional methods of extraction in liquid phase, notably aqueous extraction with controlled pH and extraction in polar solvent, optionally combined with methods of concentration by drying in vacuum or by reverse osmosis, or of concentration and purification by chromatography or by ultrafiltration.

It has also been found that certain substances isolated from said algae extracts or obtained by chemical synthesis, particularly the substances selected from the fucols, polyfucols, diphloretols, polyphloretols, bifuhalols, polyfuhalols and phloretols, have an anti-radical activity towards the superoxide radical.

Consequently, in the present description, the term "algae extracts" being used generally, covers also the active substances isolated from said extracts, or obtained by chemical synthesis.

The method used for measuring the anti-radical power is that of Winterbourn (J. Lab. Clin., Med. 85.337).

The invention will be illustrated by the following non-restrictive examples.

A. Examples of Preparation of Algae Extracts According to the Present Invention

EXAMPLE 1

100 g of *Fucus vesiculosus* are incorporated in 200 ml of water.

The mixture is ground in an "ultra turrax" type grinder for 10 mins. at room temperature.

The extraction is carried out under slight stirring for 24 hours at room temperature, and the resulting solution is filtered.

The filtrate then obtained, after elimination of water, is in powder form.

EXAMPLE 2

100 g of *Ascophyllum nodosum* are incorporated in 200 ml of water.

The mixture is ground in the same conditions as in Example 1.

The extraction is carried out under slight stirring for 12 hours at 50° C., and the resulting solution is filtered.

EXAMPLE 3

100 g of *Pelvetia canaliculata* are incorporated in a hydroalcoholic mixture constituted by 180 ml of water and 20 ml of ethyl alcohol.

The grinding is performed in the same conditions as those described in Example 1.

The extraction is carried out under slight stirring for 12 hours at 50° C., and the resulting solution is filtered.

EXAMPLE 4

100 g of *Fucus vesiculosus* are incorporated in 200 ml of water.

A grinding and an extraction are performed in the conditions defined in Example 1, then the solution is filtered.

An evaporation in vacuo is carried out on the filtrate at room temperature to obtain a perfectly dry extract.

EXAMPLE 5

100 9 of Enteromorpha are incorporated in a hydroalcoholic mixture containing 180 ml of water and 20 ml of ethanol.

A grinding is performed in the conditions defined in Example 1, followed by an extraction under slight stirring for 8 hours at 40° C., then the solution is filtered.

EXAMPLE 6

100 g of *Palmaria palmata* are incoporated in a hydroalcoholic mixture containing 180 ml of water and 20 ml of isopropyl alcohol.

A grinding is performed in the conditions defined in Example 1, followed by an extraction under slight stirring for 24 hours at 30° C., then the solution is filtered.

EXAMPLE 7

100 g of *Sargassum muticum* are incorporated in a hydroalcoholic mixture containing 100 ml of water and 100 ml of propyleneglycol.

A grinding is performed in the conditions defined in Example 1, followed by an extraction under slight stirring for 24 hours at 20° C., and the resulting solution is filtered.

EXAMPLE 8

100 g of *Ceranium rubrum* are incorporated in a hydroalcoholic mixture containing 190 ml of water and 10 ml of ethanol.

A grinding is performed in the conditions defined in Example 1, followed by an extraction under slight stirring for 24 hours at 20° C. and the resulting solution is filtered.

EXAMPLE 9

100 g of *Gracilaria verrucosa* are incorporated in a mixture constituted of 180 ml of water and 20 ml of polypropylene glycol.

A grinding is performed in the conditions defined in Example 1, followed by an extraction under slight stirring for 12 hours at 40° C., and the resulting solution is filtered.

EXAMPLE 10

100 9 of *Ulva lactuca* are incorporated in a hydroalcoholic mixture containing 160 ml of water and 40 ml of ethanol.

A grinding is performed in the conditions defined in Example 1, followed by an extraction under slight stirring for 8 hours at 50° C. and the resulting solution is filtered.

EXAMPLE 11

100 g of *Laminaria digitata* are incorporated in a hydroalcoholic mixture containing 190 ml of water and 10 ml of ethanol.

A grinding is performed in the conditions defined in Example 1, followed by an extraction under slight stirring for 48 hours at 50° C., and the resulting solution is filtered.

EXAMPLE 12

100 g of *Codium* are incorporated in a hydroalcoholic mixture containing 180 ml of water and 20 ml of ethanol.

A grinding is performed in the conditions defined in Example 1, followed by an extraction under slight stirring for 48 hours at 30° C., and the resulting mixture is filtered.

EXAMPLE 13

100 g of *Fucus vesiculosus* are immersed for about 30 mins. in a hydroalcoholic solution in order to inactivate, by saponification, the lipoxygenase and the catalase and to eliminate most of the lipids.

After washing, an extraction is carried out in 200 ml of water for 12 hours at room temperature.

The resulting extract is then centrifuged to about 3000 g and then purified in the following way:

Solid ammonium sulphate is added to the resulting centrifuged product in sufficient quantity to obtain a final concentration of 60% of the saturation at 5° C. The precipitate then eliminated by centrifuging (2000–3000 g).

Ammonium sulphate is added to the centrifuged product (80% of the saturation threshold). Once mixed, the precipitate is recovered by centrifuging. Once the traces of supernatant have been carefully eliminated, the precipitate is dissolved again in an aliquot quantity of buffer water (pH 8.5).

The resulting solution is then applied on a column filled with QAE SEPHAROSE balanced with the same buffer. The extract is eluted. The fractions containing more than 50% of the maximum activity are combined and concentrated. The reduced fraction is filtered on a SEPHACRYL S-300 gel buffered to a pH of 7.8 with a 10 mM potassium phosphate solution. The fractions containing more than 50% of the maximum activity are combined and concentrated until a phosphate concentration of 1 mM (pH 7.8) is obtained.

The material is then chomatographied on a column of hydroxyapatite buffered so that a pH of 7.8 is obtained with a 10 mM phosphate solution. After elution, the purified extract is concentrated.

B. Determination of the Anti-radical Activity of the Algae Extracts According to the Invention The anti-radical activity of the algae extracts according to the invention is determined by using Winterbourn's technique. This technique is based on the inhibition, with the enzyme, of the reduction reaction of the tetrazolium nitroblue (NBP) caused by the free superoxide radicals.

The free radicals are generated by the riboflavin in the presence of light.

Experimental Protocol

The following are introduced into a test tube:

0.2 ml of EDTA 0.1 ml of NBT 0.1 ml of enzymatic solution containing between 5 and 10 µm of protein 2.6 of phosphate buffer.

The mixture is incubated for a few minutes in front of a source of light in order to heat the reaction mixture up to around 30° C.

50 µl of riboflavin are then added, and the tubes are returned in front of the source of light. After 12 mins., the OD is read to be 560 nm against distilled water.

A control tube in which the enzyme has been replaced by distilled water is subjected to the same experimental protocol.

The inhibition percentage (Ip) of the reduction of the NBT is thus determined, using the values of OD at 580 nm obtained for the reaction tube and for the control tube, according to the formula:

$$Ip = \left(1 - \frac{OD \text{ reaction tube}}{OD \text{ control tube}}\right) \cdot 100$$

The obtained Ip value should be close to 50% of inhibition of the NBT reduction.

The results are given in NBT units per gramme of fresh algae.

An NBT unit per gramme is equal to $$\frac{10^6}{Q_{50}}$$

wherein $Q_{50}$ is the quantity of enzymes in µg causing 50% inhibition of the NBT reduction.

The anti-radical activity of the algae extracts obtained in Examples 1 to 12 was measured by using the aforedescribed method.

The results obtained are given in Table I.

As shown in said Table, the anti-radical activity varies according to the nature of the algae extract.

Very good results are obtained with the extracts of *Fucus vesiculosus* of Examples 1 and 4.

The dry extract obtained in Example 4 presents a remarkable anti-radical activity.

Very interesting results have also been obtained with extracts obtained by subjecting the filtrate of Example 1 to a concentration by ultrafiltration, by reverse osmosis and by chromatography.

TABLE I

| Algae extract according to Example | Nature of the algae used | Anti-radical activity NTB units per gramme of fresh algae |
|---|---|---|
| 1 | *Fucus vesiculosus* | 11,200 |
| 2 | *Aschophyllum nodosum* | 1,500 |
| 3 | *Pervetia canaliculata* | 1,400 |
| 4 | *Fucus vesiculosus* | 120,000 |
| 5 | *Enteromorpha* | 1,300 |
| 6 | *Palmaria palmata* | 260 |
| 7 | *Sargassus muticum* | 600 |
| 8 | *Ceramium rubrum* | 400 |
| 9 | *Gracilaria verrucosa* | 100 |
| 10 | *Ulva lactuca* | 150 |
| 11 | *Laminaria digitata* | 100 |
| 12 | *Codium* | 200 |

The protective effect of the algae extracts according to the invention, against degradation of the desoxyribose (D.R.) of radical origin, has also been tested.

Generally speaking, the "desoxyribose" test is conducted in order to determine indirectly the production of radical oxygenous metabolites within the biological system by measuring the production of MDA).

This test can be performed in a relatively easy way, and it gives the possibility of obtaining various quantitative information, on the anti-radical power of a molecule in vitro, by its ability to inhibit more or less completely the degradation of the desoxyribose of radical origin.

It has thus been determined that the rate of protection of the algae extracts according to the invention was relatively high. For example, the algae extract according to Example 4 has a rate of protection of 84, 81, 79, 66 and 38% for rates of incorporation (volume/volume) of 10, 8, 5, 2 and 1% respectively.

The aforementioned tests in vitro were completed with a test in vivo, with a view to determining the anti-radical activity of the algae extracts according to the invention, during a lipid peroxidation induced in cultivated human fibroblasts by the hypoxanthine-xanthine oxidase stress.

More precisely, the protective effects of the algae extracts according to the invention have been studied against damages induced by a stress generating superoxide ions in the extra-cellular medium.

This study has shown that an algae extract according to the invention can, under certain conditions, inhibit the peroxidation radical process of the membranar lipids of cultivated human fibroblasts.

By way of example, it can be indicated here that the algae extract according to Example 4, makes it possible to obtain a high rate of inhibition of the lipid peroxidation induced in the fibroblasts (about 80%) for a rate of incorporation in the fibroblasts incubation medium of 10% (volume/volume).

This inhibition rate remains significant (about 40%) for a rate of incorporation of 2% (volume/volume).

From the tests in vivo it can be thought that the anti-radical effect of the algae extracts according to the invention results from the intercepting of the superoxide radicals generated in the extra-cellular medium.

It has also been shown, with the aforementioned tests, that certain active substances isolated from algae extracts, or obtained by chemical synthesis, particularly the substances selected among the fucols, polyfucols, diphloretols, polyphloretols, bifuhalols, polyfuhalols, phloterols had an anti-radical activity.

These active substances are easy to determine for the man skilled in the art.

However, the tests carried out by the applicant have shown that, among the substances isolated from algae extracts and selected from the aforementioned families of compounds, only certain compounds of specific chemical structure are active.

Generally speaking, these active compounds are fucols, polyfucols, diphloretols, polyphloretols, bifuhalols, polyfuhalols, phloterols (of which the chemical structure is known) which have on each aromatic ring at least one hydroxyl group, and provided that, when an aromatic ring has at least two hydroxyl groups, these groups are not in meta- position with respect to each other, except in the case where three hydroxyl groups occupy respectively three successive positions on the aromatic ring.

Accordingly, in the case of the fucols, the active substances are the compounds of formula:

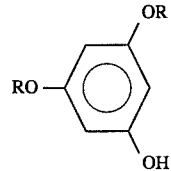

in which R is, in known manner, an alkyl group or a sugar, as well as the compounds derived therefrom by replacement of one or several hydrogen atoms on the aromatic ring with one or several halogen atoms, or one or several nitro groups.

Among the active substances isolated from algae extracts according to the invention, the most advantageous compounds are the fucohalols and their derivatives. These compounds have the general formula:

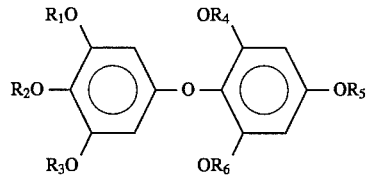

in which $R_1$, $R_2$, $R_3$, $R_4$, $R_5$, $R_6$ can represent a hydrogen atom, an alkyl group or a sugar in the abovementioned conditions.

It has been especially noted that the compounds, in which $R_1$, $R_2$, $R_3$ and optionally one of the groups $R_4$, $R_5$, $R_6$ represent a hydrogen atom, had a remarkable anti-radical activity.

The algae extracts according to the invention are not toxic (administered orally, the $LD_{50}$ is higher than 10 g/kg). The tests for skin and eye irritation have shown that these extracts are not irritant.

Generally speaking, the algae extracts according to the invention can be used for preparing antiradiation, anticleroderma pharmaceutical compositions, or are useful for the treatment of skin lesions and burns, skin dehydration, skin atony or even purulent dermatitis.

To this effect, the form of administration selected will allow an external application. The extract used may be pure or diluted to as much as 5%.

In that form, the object of the present invention is to cover a method for the therapeutic treatment of the human or animal body, characterized in that it comprises administering a therapeutically efficient quantity of at least one algae extract obtained by extraction in liquid phase or of at least one active substance isolated from said extract, or obtained by chemical synthesis, selected in particular among the fucols, polyfucols, diphloretols, polyphloretols, bifuhalols, polyfuhalols, diphloretols, polyphloretols, bifuhalols, polyfuhalols and phloretols.

The cosmetic compositions incorporating algae extracts according to the invention are particularly suitable for protecting the skin due in particular to the protection afforded by the nucleic acids, the collagen of hyaluronic acid, membranar lipids and proteins.

It is notably proposed to develop cosmetic compositions intended for giving protection against the phototoxic reactions, UV aggression, or for treating actinic erythema.

Such cosmetic compositions are also useful for protecting the living keratin substances constituting the skin, the scalp or the hair.

The algae extracts according to the invention can also be incorporated in cosmetic compositions for protecting the other ingredients against oxidation.

In the field of food products, the invention makes it possible to produce antioxidant compositions, efficient against the peroxidation of lipids, the denaturation of the enzymes or the depolymerization of the polysaccharides. It is also possible with these compositions to preserve the quality of fruits and vegetables.

In the agricultural field, the invention makes it possible to prepare compositions intended for improving the preservation of seeds, fruits, vegetables, tubercles and ensilages or to protect germinations or crops against oxidation reactions due to various stress (hydric, cold, osmotic, lack of nutrient elements, pollutions, pesticide treatments).

Examples of compositions according to the invention are given hereafter by way of illustration.

Treatment cream:

| | |
|---|---|
| Cyclogol NI | 10% |
| "Carnation" mineral oil | 15% |
| Lanolin oil | 0.25% |
| Oleate of polypropyleneglycol 2000 | 5% |
| Aqueous extract of Fucus vesiculosus | 10% |
| Perfume | 0.2% |
| Paraben | 0.1% |
| Water | 59.45% |

The NI cyclogol of the company WITCO is a mixture of cetearyl alcohol and of Ceteareth 20.

Schampoo:

| | |
|---|---|
| Triethanolamine lauryl sulphate | 15% |
| Coprah diethanolamide | 2% |
| Aqueous extract of Ascophyllum nodosum | 4% |
| Honeysuckle perfume | 0.2% |
| Paraben | 0.1% |
| Water | 78.7% |

Foam bath:

| | |
|---|---|
| Sulfosuccinic acid hemiester | 45% |
| Coprah diethanolamide | 2.5% |
| Aqueous extract of Ulva lactuca | 10% |
| EDTA 4 Na | 1% |
| Perfume | 0.3% |
| Paraben | 0.1% |
| Coloring agent E 131 | 0.01% |
| Water | 41.1% |

Sun lotion:

| | |
|---|---|
| Giv-Tan F (Givaudan) | 2% |
| Oleate of polypropylene 2000 | 25% |
| Hydroalcoholic extract of Fucus vesiculosus | 10% |
| Ethanol | 62.7% |
| Perfume | 0.3% |

Cleansing milk:

| | |
|---|---|
| Steapyrium chloride | 1% |
| Carnation oil | 4% |
| Glycerol monostearate | 2% |
| Glycerin | 4% |
| Glycolic extract of Ceranium rubrum | 4% |
| Perfume | 0.3% |
| Water | 84.7% |

Shaving foam:

| | |
|---|---|
| Stearic acid | 6.8% |
| Triethenolamine | 3.7% |
| Propyleneglycol 2000 | 0.6% |
| Lauramid | 0.5% |
| Distearate of polyethyleneglycol 150 | 0.2% |
| Propyleneglycol stearate | 1% |
| Glycolic extract of Pelvetia canaliculata | 3% |
| Perfume | 0.4% |
| Glycerol | 1% |
| Water | 82.8% |

Antiradiation cream:

| | |
|---|---|
| Glycerol monostearate | 5% |
| Stearine | 3.6% |
| Liquid paraffin | 7% |
| Cetyl palmitate | 0.4% |
| Triethanolamine alginate | 0.8% |
| Glycolic extract of Fucus | 9% |
| Triethanolamine | 0.4% |
| Perfume | 0.1% |
| Paraben | 0.1% |
| Purified and deionized water | 73.6% |

This cream can be applied morning, noon and night in thick layers over and around the treated areas. The cream will be allowed to sink in by rubbing slightly.

Antisenescence cream:

| | |
|---|---|
| Cyglocol NI | 4.5% |
| Bees' wax | 13% |
| Glycolic extract of ascophyllum | 12% |
| Lanolin | 3% |
| Carnation mineral oil | 12% |
| Borax | 1.5% |
| Perfume | 0.2% |
| Paraben | 0.1% |
| Water | 53.7% |

Foliar fertilizer Zn:

| | |
|---|---|
| Water | 34.6% |
| Zinc sulphate (with 21% Zn) | 23% |
| Potash | 0.4% |
| Magnesium chloride with 22.5% MgO | 12% |
| Betain extracts (dosing 10% betains) | 20% |
| Aqueous extract of fucus | 10% |

Foliar fertilizer MnCu:

| | |
|---|---|
| Copper sulphate (25% Cu) | 6.8% |
| Manganese sulphate (30.8% Mn) | 2.7% |
| Magnesium chloride (22.5% MgO) | 24.4% |
| Betain extracts (dosing 10% betains) | 16.5% |
| Aqueous extract of Fucus | 49.6% |

Cut flowers preserving agent:

| | |
|---|---|
| Aqueous extract of Fucus | 5 to 50% |
| Cobalt salt (Copper sulphate, chloride, cobalt nitrate) | 0.2 mM |
| Water (s.q.f.) | |

| Fruits, vegetables and tubercles preserving agent: | |
| --- | --- |
| Aqueous extract of Fucus | 10 to 95% |
| ascorbic acid | 5–500 mM |
| Polyphosphate acid | 0.1–5% |
| Dietetic bar: | |
| Dry extract of Fucus | 200 mg |
| Crystalline cellulose | 47 mg |
| Dextrin | 5 mg |
| Lactose | 20 mg |
| Carboxymethylcellulose | 5 mg |
| Talc | 3 mg |
| Dietetic drink: | |
| Extract of Fucus | 1 to 20% |
| Perfume (lemon, orange, ...) | 0.5 to 1.0% |
| Citric acid | 0.5 to 1.0% |
| Water (s.q.f. 1000). | |

The algae extracts according to the invention present numerous advantages. Beside a very strong anti-radical activity, said extracts, or the compounds isolated therefrom, are found to have a very great stability, very much greater than that of the compounds such as the dismutase superoxides. Moreover, their low molecular weight helps the penetration through the skin. Finally, said extracts show remarkable innocuity.

I claim:

1. A method of providing anti-radical activity towards a superoxide radical in a composition, comprising admixing to the composition an effective amount of at least one algae extract to increase the antiradical activity towards the superoxide radical of the composition, wherein said algae is selected from the group consisting of *Fucus vesiculosus,* *Ascophyllum nodosum, Pelvetia canaliculata, Sargassum muticum, Ceramium rubrum* and *Palmaria palmata.*

2. The method of claim 1, wherein the composition is selected from the group consisting of pharmaceutical, cosmetic, food, and agricultural compositions.

3. The method of claim 1, wherein the algae extract is obtained by extraction in the liquid phase.

4. The method of claim 1, wherein the algae extract is obtained by aqueous extraction under controlled pH.

5. The method of claim 1, wherein the algae extract is obtained by extraction in a polar solvent.

6. The method of claim 1, wherein the algae extract is obtained by extraction in the liquid phase followed by evaporation in vacuo.

7. A method of providing anti-radical activity towards a superoxide radical in a composition, comprising admixing to the composition an effective amount of an extract from a brown algae to increase the antiradical activity towards the superoxide radical of the composition, wherein the brown algae is *Fucus vesiculosus.*

8. The method of claim 7, wherein the composition is selected from the group consisting of pharmaceutical, cosmetic, food and agricultural compositions.

9. The method of claim 7, wherein the algae extract is obtained by extraction in the liquid phase.

10. The method of claim 7, wherein the algae extract is obtained by aqueous extraction under controlled pH.

11. The method of claim 7, wherein the algae extract is obtained by extraction in a polar solvent.

12. The method of claim 7, wherein the algae extract is obtained by extraction in the liquid phase followed by evaporation in vacuo.

* * * * *